United States Patent [19]

Fraser

[11] Patent Number: 5,741,336
[45] Date of Patent: Apr. 21, 1998

[54] MAGNETICALLY SECURED HAIRPIECES

[76] Inventor: William A. Fraser, 3001 Audubon Ter., N.W., Washingtn, D.C. 20008

[21] Appl. No.: 703,912

[22] Filed: Aug. 27, 1996

[51] Int. Cl.$^6$ .................................................. A61F 2/10
[52] U.S. Cl. .......................................... 623/15; 132/53
[58] Field of Search .............................. 623/15, 66, 33, 623/36; 132/53, 54, 201

[56] References Cited

U.S. PATENT DOCUMENTS

| | | |
|---|---|---|
| 3,476,122 | 11/1969 | Zaupa . |
| 3,516,422 | 6/1970 | Bechtold et al. . |
| 3,662,766 | 5/1972 | Maassen et al. ............ 132/53 |
| 3,694,819 | 10/1972 | Meyer ........................ 623/15 |
| 3,760,818 | 9/1973 | Schweifer . |
| 3,811,425 | 5/1974 | Widdifield ................... 623/15 |
| 3,908,674 | 9/1975 | Kessler ....................... 132/53 |
| 4,155,370 | 5/1979 | Nemoto . |
| 4,168,713 | 9/1979 | Agiotis . |
| 4,352,960 | 10/1982 | Dormer et al. ............. 179/107 BC |
| 4,736,747 | 4/1988 | Drake ......................... 128/419 R |
| 4,825,886 | 5/1989 | Allen . |
| 5,005,594 | 4/1991 | Dunagan . |
| 5,419,345 | 5/1995 | Kadymir . |
| 5,507,835 | 4/1996 | Jore ............................ 623/36 |
| 5,545,224 | 8/1996 | Israelsen .................... 623/15 |

*Primary Examiner*—John G. Weiss
*Assistant Examiner*—Bruce E. Snow
*Attorney, Agent, or Firm*—Papan Devnani; Thomas A. Powers; Chandrakant Shroff

[57] ABSTRACT

The invention is a system for securing a hairpiece to a defined portion of a person's scalp. The system comprises:

a) a plurality of first magnets adapted to be surgically implanted between the skin of the defined portion of the person's scalp and the person's skull, said first magnets being shaped like flat disks and coated with a hypoallergenic material; and b) a hairpiece adapted to cover the defined portion of the person's scalp, said hairpiece comprising:
  (i) a base fabric;
  (ii) a plurality of fibers secured to one side of the base fabric; and
  (iii) a plurality of second magnets, said second magnets being fastened to the other side of the base fabric. After the first magnets are implanted beneath the scalp, the hairpiece is secured to the scalp by magnetic attraction between the first and second magnets.

22 Claims, 3 Drawing Sheets

MAGNETICALLY SECURED HAIRPIECES

FIELD OF THE INVENTION

The field of the invention is directed towards a means of fastening an artifical hairpiece, commonly referred to as a wig or toupee, onto a person's head. More specifically, the invention relates to a method of fastening a hairpiece in place without requiring the use of adhesives.

BACKGROUND OF THE INVENTION

Many people around the world suffer from partial or total baldness. Some people view this as being an undesirable or unattractive feature, leading to a burgeoning industry devoted to methods of solving this problem. The most common means of hiding baldness is through the use of an artificial hairpiece. A hairpiece typically comprises a base fabric to which fibers are securely anchored by one end. The base fabric may be a woven fabric, a knitted fabric, or an air- and moisture-permeable polymeric film. A laminate of a woven or knitted fabric and a breathable polymeric film is also usable. The base fabric should be made so that it closely conforms to the shape of the human head. The fibers should resemble human hair, and may be made from natural human or animal hair, from silk or other natural fibers, or from nylon or other synthetic polymer fibers. The fibers should be woven, sewn, tied, or adhesively fastened to one side of the base fabric.

A partially or totally bald person then wears the hairpiece on his head with the side of the base fabric to which the fibers are secured facing away from his scalp to create the illusion of a full head of hair. The hairpiece may simply be worn, but if the bald person expects to be subjected to adverse weather conditions, such as high winds, or to participate in strenuous physical activity, he must face the embarrassing possibility that the hairpiece will come loose.

The usual means of preventing a hairpiece from coming loose is to coat the inner surface of the hairpiece and/or the scalp with an adhesive substance, and glueing the hairpiece to the scalp. However, this can be messy and can cause allergic reactions in some people, and a better method of adhering hairpieces to a person's head is therefore desired.

A doctor in the state of New York has invented a surgical method of holding a hairpiece in place. Holes are drilled in a bald person's skull and metal pegs are implanted in the holes. When the pegs become permanently bonded to the bone, the hairpiece may be attached to the pegs by means of snaps in the wig. This procedure has the disadvantage of requiring an extended healing time, causing considerable discomfort and pain, and requiring a hazardous operation to drill into the skull.

It is an object of this invention to provide a system for holding a hairpiece in place which avoids the disadvantages described above, and a method of using the same.

SUMMARY OF THE INVENTION

This invention relates to an improved method of securing a hairpiece to a bald or partially bald person's scalp, and to a system for use in carrying out the method. The method involves the steps of implanting magnets beneath the skin of a bald person's scalp, and then magnetically adhering a hairpiece having a magnetized base fabric to the surgically implanted magnets. This holds the hairpiece to the person's scalp firmly, but temporarily. The base fabric may be made of a magnetic material, or it may be made of a nonmagnetic material and magnetized by fastening magnets to the base fabric.

DETAILED DESCRIPTION OF THE DRAWINGS

DETAILED DESCRIPTION OF THE INVENTION

Figure 1:
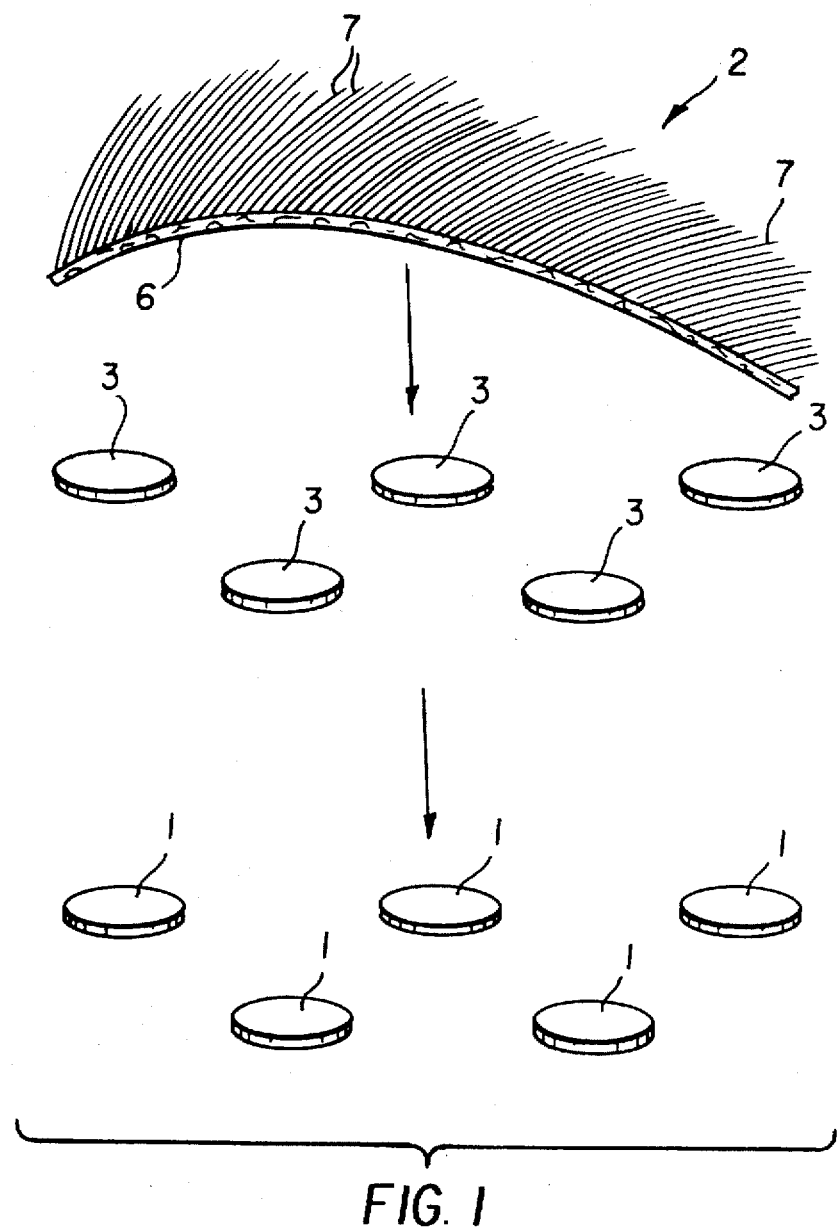
FIG. 1 is an illustration of the components of one embodiment of the system for securing a hairpiece to a person's head described herein.

The invention relates to a system or kit which may be used to carry out the method of the invention. The elements of the system or kit are illustrated in FIG. 1. The system or kit comprises a set of first magnets 1, where magnets 1 are adapted to be implanted between the skin of a bald person's scalp and the bald person's skull, a hairpiece 2, and a set of second magnets 3. The hairpiece 2 comprises a base fabric 6 and a plurality of fibers 7 which resemble natural hair secured to a first side of the base fabric. Each of the second magnets 3 is adapted to be simultaneously fastened to a second side of the base fabric 6 of the hairpiece 2 and magnetically adhered to a first magnet 1 which has been implanted beneath a bald person's scalp.

Figure 2A:
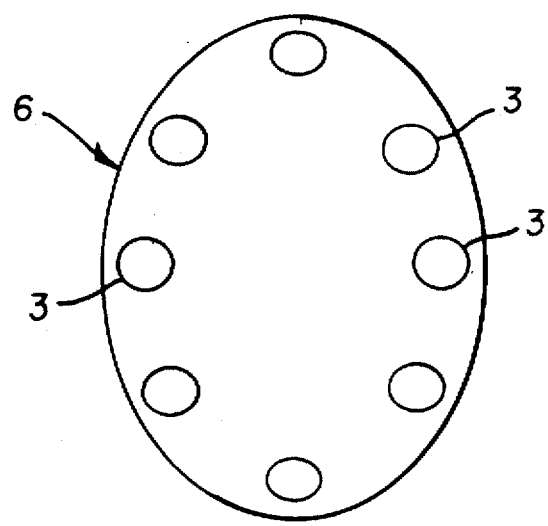
FIGS. 2a and 2b illustrate hairpieces with magnets attached to their undersides in defined patterns.
Figure 2B:
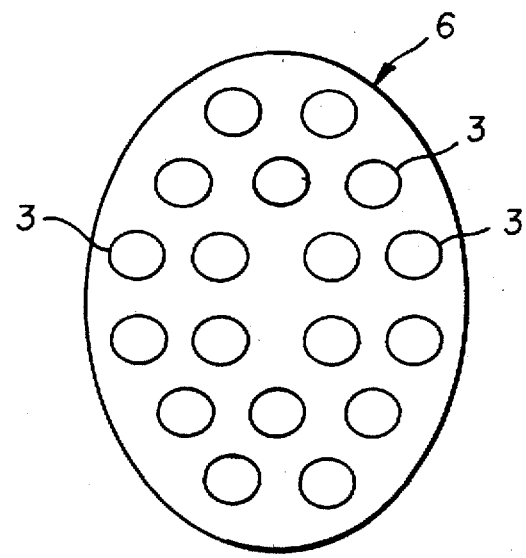
Figure 3:
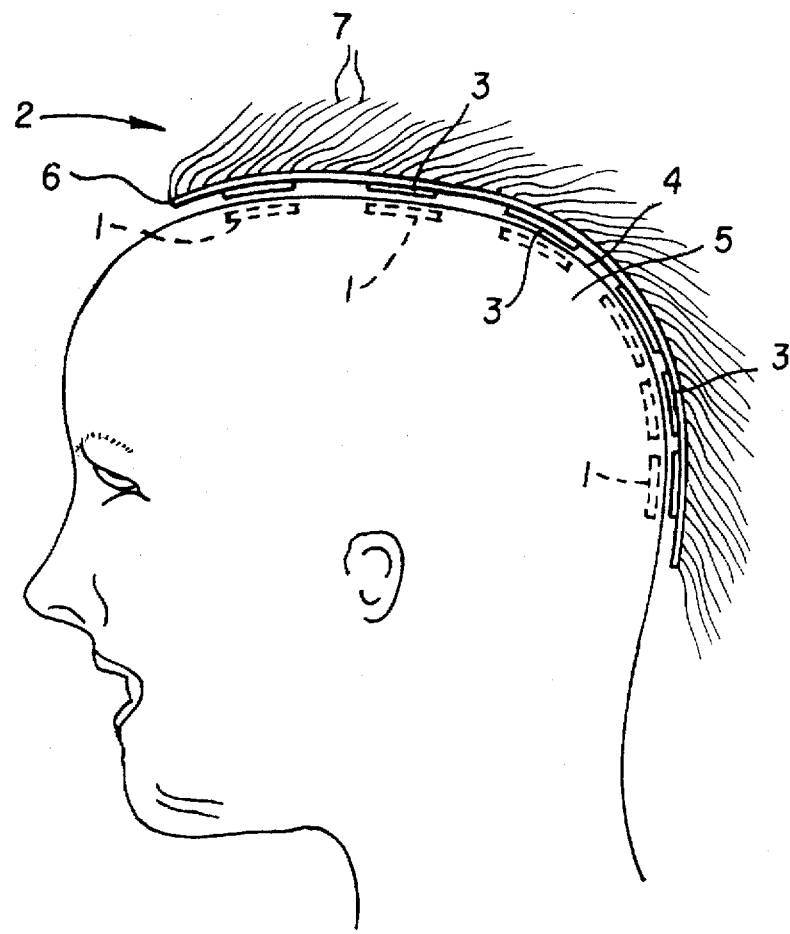
FIG. 3 shows the hairpiece-securing system of the present invention being used to secure a hairpiece to a person's head.

Preferably, the second magnets 3 are adapted to be fastened to the hairpiece in a defined pattern. For example, the magnets 3 may be evenly spaced about the outer perimeter of the hairpiece, as shown in FIG. 2a. Alternatively, the magnets 3 may be arranged in an ordered array or pattern which covers the entire hairpiece, as shown in FIG. 2b. Magnets 1 may then be implanted between the bald person's scalp 4 and the bald person's skull 5. The magnets 1 should be implanted in a pattern which complements the pattern in which magnets 3 have been arranged on the hairpiece in such a way that, when the hairpiece is correctly positioned on the bald person's scalp, each magnet 3 on the hairpiece is positioned directly over one and only one surgically implanted magnet 1. FIG. 3 illustrates correct positioning of magnets 1, hairpiece 2, and magnets 3 on a human head.

First magnets 1 are usually made of small, flat pieces of ferrous metal. These magnets are preferably shaped like circles, ovals, or polygons having only obtuse angles (for example, pentagons or hexagons). However, they can be formed in a variety of other shapes, if desired. Also, magnets which are bent in a way which allows them to conform to the shape of the skull may be used instead of flat magnets. Magnets 1 preferably have a maximum width of ½ inch or less, although larger sizes may be used if desired. It is also possible to use two or more different sizes of magnets at once. For example, small magnets can be implanted beneath the scalp at places where the underlying skull is strongly curved (i.e., the crown of the head), while larger magnets can be implanted beneath the scalp at places where the underlying skull is flatter (i.e., the sides of the head). The most preferred magnets 1 for use in the invention will be disk-shaped magnets like those shown in FIG. 1, having a maximum diameter of ½ inch.

Since they are intended to be implanted in a human body, it is preferred that magnets 1 be coated with a hypoallergenic material. This material is preferably a polymer which is not hydrolyzed or otherwise degraded by blood and similar non-gastric biological fluids. Aliphatic polyamides (nylons), which are commonly used medically as nonabsorbable sutures, would seem to be suitable. Magnets 1 may be coated with a hypoallergenic ceramic or metallic material instead of with a plastic, if desired. Alternatively, magnets 1 may be made from disk-shaped pieces of a flexible polymeric material, preferably a hypoallergenic polymer, which contains a high concentration of magnetized particles. This allows the magnets to bend after being implanted beneath a person's scalp so that they can conform to the shape of the person's skull.

The method of adhering a hairpiece to a person's head involves an initial step of surgically implanting a set of magnets 1 between the skin of the person's scalp and the person's skull. A hairpiece 2 adapted to cover the defined portion of the person's scalp is then obtained, where said hairpiece comprises a base fabric and a plurality of fibers having one end secured to one side of the base fabric. Next, a second set of magnets 3 is fastened to the other side of the base fabric of the hairpiece. The hairpiece is then fastened to the person's scalp by covering the desired portion of the person's scalp with the hairpiece and adhering the surgically implanted magnets to the magnets fastened to the hairpiece. The magnetic attraction holding the hairpiece to the person's head is firm, but temporary.

The second set of magnets 3 should be fastened to the hairpiece in such a way that when the hairpiece is positioned on the desired portion of the person's scalp, each magnet secured to the hairpiece directly overlies one of the surgically implanted magnets. To ensure this, it is best to implant the first magnets beneath the scalp in a first defined pattern, and to fasten the second magnets to the hairpiece in a second defined pattern which is complementary to the first defined pattern. Preferably, the second defined pattern is a mirror image of the first defined pattern. If this is done, there will be a precise one-to-one correspondence between the first magnets and the second magnets when the hairpiece is positioned on the person's head.

If desired, the first magnets 1 or the second magnets 3, but not both the first and second magnets, may be replaced with non-magnetized pieces of ferrous material. For example, the first magnets 1 may be replaced with pieces of non-magnetized ferrous material adapted to be implanted beneath a person's scalp. Usually, the pieces of ferrous material will be pieces of ferrous metal. Preferably these pieces of ferrous metal should be coated with a hypoallergenic polymer which does not degrade in the presence of non-gastric biological fluids. Alternatively, pieces of a polymeric material containing a high concentration of non-magnetized ferrous particles may be used as pieces of non-magnetized ferrous material. The pieces of ferrous material are implanted beneath a person's scalp. A set of magnets 3 which have been fastened to a hairpiece 2 may then be magnetically adhered to these pieces of ferrous material, exactly as previously described. This secures hairpiece 2 to the person's scalp. However, it must be noted that the attraction between a piece of non-magnetized ferrous material and a magnet is weaker than that between two magnets.

Alternatively, the second magnets 3 may be replaced with pieces of ferrous material. Usually, the pieces of ferrous material which are used to replace the second magnets will be pieces of ferrous metal. Alternatively, the pieces of non-magnetized ferrous material used to replace the second magnets may be pieces of a polymeric material containing a high concentration of non-magnetized ferrous particles. These pieces of ferrous metal are secured to the base fabric of hairpiece 2. The pieces of ferrous metal are then magnetically adhered to magnets 1 which have been implanted beneath a person's scalp, using the previously described procedure.

Figure 4:
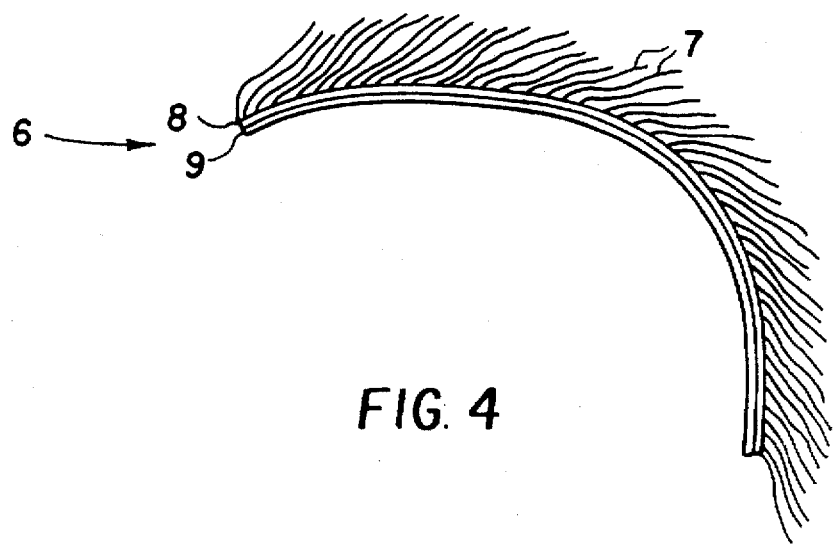
FIG. 4 shows a wig made from a base fabric comprising a laminate having one layer of a magnetic material, and one layer of a nonmagnetic material.

Finally, the second magnets may be omitted entirely if the base fabric of the hairpiece comprises a magnetic material as shown in FIG. 4. Such a base fabric would comprise an air- and moisture-permeable polymeric sheet containing a high concentration of magnetized particles. Preferably, the base fabric 6 comprises a laminate of an air- and moisture-permeable polymeric sheet 8 containing a high concentration of magnetized particles and a woven or knitted fabric 9 adhered to one side of the polymeric sheet. One end of each of a plurality of fibers resembling natural hair is anchored to the woven or knitted fabric. A plurality of magnets 1 are implanted beneath a person's scalp. A hairpiece comprising a base fabric comprising an air- and moisture-permeable polymeric sheet containing a high concentration of magnetized particles is positioned on the person's scalp, over implanted magnets 1. The magnetized particles in the base fabric will be magnetically attracted to implanted magnets 1, fastening the hairpiece firmly, but temporarily, to the person's head. It is possible to use non-magnetized ferrous particles instead of magnetized particles in the base fabric of the hairpiece. The non-magnetized ferrous particles are attracted to implanted magnets in the same way as magnetized particles.

If desired, the magnets may be anchored in position when they are implanted beneath the scalp to prevent migration of the magnets. It is preferred to do this without drilling into the bone of the skull. The magnets may be adhesively secured to the bone of the skull. The magnets may have holes that allow them to be secured to the soft tissues adhering to the skull, possibly by suturing. However, it is possible to provide posts on the magnets which may be fitted into holes drilled into the skull.

What is claimed is:

1. A method of securing a hairpiece to a defined portion of a person's scalp, comprising the steps of:

a) obtaining a plurality of hypoallergenic first magnets;

b) implanting the first magnets between the skin of the defined portion of the person's scalp and the person's skull;

c) obtaining a hairpiece adapted to cover the defined portion of the person's scalp, said hairpiece comprising a base fabric and a plurality of fibers having one end secured to one side of the base fabric;

d) obtaining a plurality of second magnets;

e) fastening the second magnets to the side of the base fabric of the hairpiece other than the side to which the fibers are adhered; and f) fastening the hairpiece to the person's scalp by covering the desired portion of the person's scalp with the hairpiece and magnetically adhering the surgically implanted first magnets to the second magnets fastened to the hairpiece;

with the proviso that the second magnets are fastened to the hairpiece in such a way that when the hairpiece is positioned on the desired portion of the person's scalp, each of the second magnets directly overlies one of the first magnets.

2. The method of claim 1, wherein the first magnets are shaped like flat disks having a diameter of not more than ½ inch.

3. The method of claim 1, wherein the first magnets are made of a ferrous metal which has been coated with a hypoallergenic material.

4. The method of claim 3, wherein the hypoallergenic material is a polymer which will not break down upon exposure to biological fluids.

5. The method of claim 3, wherein the hypoallergenic material is a ceramic material or a metallic material.

6. The method of claim 4, wherein the polymer is an aliphatic polyamide.

7. The method of claim 1, wherein the second magnets are fastened to the base fabric of the hairpiece so that the second magnets are evenly spaced along the periphery of the base fabric.

8. The method of claim 1, wherein the second magnets are fastened to the base fabric of the hairpiece so that the second magnets are arranged in a patterned array on the base fabric.

9. The method of claim 1, wherein the first magnets are flexible magnets which are adapted to conform to the shape of the person's skull after implantation between the person's scalp and the person's skull.

10. A method of securing a hairpiece to a defined portion of a person's scalp, comprising the steps of:
    a) obtaining a plurality of magnets, said magnets being coated with a hypoallergenic material;
    b) implanting the magnets between the skin of the defined portion of the person's scalp and the person's skull;
    c) obtaining a hairpiece adapted to cover the defined portion of the person's scalp, said hairpiece comprising a base fabric and a plurality of fibers having one end secured to one side of the base fabric;
    d) obtaining a plurality of pieces of ferrous material;
    e) fastening the pieces of ferrous material to the side of the base fabric of the hairpiece other than the side to which the fibers are adhered; and
    f) fastening the hairpiece to the person's scalp by covering the desired portion of the person's scalp with the hairpiece and magnetically adhering the surgically implanted magnets to the pieces of ferrous material fastened to the hairpiece;
    with the proviso that the pieces of ferrous material are fastened to the hairpiece in such a way that when the hairpiece is positioned on the desired portion of the person's scalp, each of the pieces of ferrous material directly overlies one of the magnets.

11. A method of securing a hairpiece to a defined portion of a person's scalp, comprising the steps of:
    a) obtaining a plurality of pieces of hypoallergenic ferrous material;
    b) implanting the pieces of ferrous material between the skin of the defined portion of the person's scalp and the person's skull;
    c) obtaining a hairpiece adapted to cover the defined portion of the person's scalp, said hairpiece comprising a base fabric and a plurality of fibers having one end secured to one side of the base fabric;
    d) obtaining a plurality of magnets;
    e) fastening the magnets to the side of the base fabric of the hairpiece other than the side to which the fibers are adhered; and
    f) fastening the hairpiece to the person's scalp by covering the desired portion of the person's scalp with the hairpiece and magnetically adhering the surgically implanted pieces of ferrous material to the magnets fastened to the hairpiece;
    with the proviso that the magnets are fastened to the hairpiece in such a way that when the hairpiece is positioned on the desired portion of the person's scalp, each of the magnets directly overlies one of the pieces of ferrous material.

12. A system for securing a hairpiece to a defined portion of a person's scalp, said system comprising:
    a) a plurality of first magnets adapted to be surgically implanted between the skin of the defined portion of the person's scalp and the person's skull, said first magnets being shaped like flat disks and coated with a hypoallergenic material; and
    b) a hairpiece adapted to cover the defined portion of the person's scalp, said hairpiece comprising:
        (i) a base fabric;
        (ii) a plurality of fibers having one end secured to one side of the base fabric; and
        (iii) a plurality of second magnets, said second magnets being fastened to the side of the base fabric of the hairpiece other than the side to which the fibers are adhered;
    further characterized in that said second magnets are magnetically attracted to said first magnets.

13. The system of claim 12, wherein the first magnets are made of a ferrous metal which has been coated with a hypoallergenic material.

14. The system of claim 13, wherein the hypoallergenic material is a polymer which will not break down upon exposure to biological fluids.

15. The system of claim 13, wherein the hypoallergenic material is a ceramic material or a metallic material.

16. The system of claim 14, wherein the polymer is an aliphatic polyamide.

17. The system of claim 12, wherein the first magnets are flexible magnets which are adapted to conform to the shape of the person's skull after implantation between the person's scalp and the person's skull.

18. A system for securing a hairpiece to a defined portion of a person's scalp, said system comprising:
    a) a plurality of magnets adapted to be surgically implanted between the skin of the defined portion of the person's scalp and the person's skull, said magnets being shaped like flat disks and coated with a hypoallergenic material; and
    b) a hairpiece adapted to cover the defined portion of the person's scalp, said hairpiece comprising:
        (i) a base fabric;
        (ii) a plurality of fibers having one end secured to one side of the base fabric; and
        (iii) a plurality of pieces of ferrous material, said pieces of ferrous material being fastened to the side of the base fabric of the hairpiece other than the side so which the fibers are adhered;
    further characterized in that said pieces of ferrous material are magnetically attracted to said magnets.

19. A system for securing a hairpiece to a defined portion of a person's scalp, said system comprising:
    a) a plurality of pieces of hypoallergenic ferrous material adapted to be surgically implanted between the skin of the defined portion of the person's scalp and the person's skull; and
    b) a hairpiece adapted to cover the defined portion of the person's scalp, said hairpiece comprising:
        (i) a base fabric;
        (ii) a plurality of fibers having one end secured to one side of the base fabric; and
        (iii) a plurality of magnets, said magnets being fastened to the side of the base fabric of the hairpiece other than the side to which the fibers are adhered;

further characterized in that said magnets are magnetically attracted to said pieces of ferrous material.

20. A method of securing a hairpiece to a defined portion of a person's scalp, comprising the steps of:
  a) obtaining a plurality of first magnets, said first magnets being coated with a hypoallergenic material;
  b) implanting the first magnets between the skin of the defined portion of the person's scalp and the person's skull;
  c) obtaining a hairpiece adapted to cover the defined portion of the person's scalp, said hairpiece comprising a magnetized base fabric and a plurality of fibers having one end secured to one side of the base fabric; and
  d) placing the hairpiece on the defined portion of the person's scalp with the side of the base fabric to which the plurality of fibers are secured facing away from the scalp so that the base fabric is magnetically attracted to the implanted first magnets.

21. The method of claim 20, where the base fabric is made of a nonmagnetic material which has been magnetized by fastening a set of second magnets to the side of the base fabric other than the side to which the plurality of fibers are secured.

22. The method of claim 20, where the base fabric is made of a magnetic material, or of a laminate having at least one layer of a magnetic material.

* * * * *